(12) United States Patent
Johnson et al.

(10) Patent No.: US 10,188,317 B2
(45) Date of Patent: Jan. 29, 2019

(54) MEASURING RESPIRATORY MECHANICS PARAMETERS USING PERTURBATIONS

(71) Applicants: Arthur T. Johnson, Darlington, MD (US); Jafar Vossoughi, Brookeville, MD (US)

(72) Inventors: Arthur T. Johnson, Darlington, MD (US); Jafar Vossoughi, Brookeville, MD (US)

(*) Notice: Subject to any disclaimer, the term of this patent is extended or adjusted under 35 U.S.C. 154(b) by 565 days.

(21) Appl. No.: 14/815,466

(22) Filed: Jul. 31, 2015

(65) Prior Publication Data

US 2016/0038057 A1 Feb. 11, 2016

Related U.S. Application Data

(60) Provisional application No. 62/033,506, filed on Aug. 5, 2014.

(51) Int. Cl.
*A61B 5/08* (2006.01)
*A61B 5/087* (2006.01)
*A61B 5/085* (2006.01)
*A61B 5/097* (2006.01)
*A61B 5/091* (2006.01)

(52) U.S. Cl.
CPC ............ *A61B 5/087* (2013.01); *A61B 5/08* (2013.01); *A61B 5/085* (2013.01); *A61B 5/091* (2013.01); *A61B 5/097* (2013.01)

(58) Field of Classification Search
CPC ........... A61B 5/08; A61B 5/085; A61B 5/087; A61B 5/091; A61B 5/097
See application file for complete search history.

(56) References Cited

U.S. PATENT DOCUMENTS

| 6,066,101 | A | 5/2000 | Johnson et al. | |
| 9,895,082 | B2 | 2/2018 | Johnson et al. | |
| 2009/0301486 | A1* | 12/2009 | Masic | A61B 5/08 |
| | | | | 128/204.21 |
| 2011/0273299 | A1* | 11/2011 | Milne | A61B 5/0803 |
| | | | | 340/573.1 |
| 2011/0282228 | A1* | 11/2011 | Shiner | A61B 5/085 |
| | | | | 600/534 |

(Continued)

OTHER PUBLICATIONS

Lausted et al., "Respiratory resistance measured by an airflow perturbation device", IOP Publishing Ltd, 1999, pp. 21-35.

(Continued)

*Primary Examiner* — Puya Agahi
(74) *Attorney, Agent, or Firm* — Edell, Shapiro & Finnan, LLC

(57) ABSTRACT

According to one embodiment of the present invention, a method of determining respiratory parameters comprises determining a ratio of pressure changes to flow changes induced in the breathing of a patient by an airflow perturbation device at each of a plurality of perturbation frequencies to form a dataset. Resistance, compliance, and inertance parameters of a model of a respiratory system are determined by comparing a predicted frequency dependence of the model to the dataset. Embodiments of the present invention further include a system and computer program product for determining respiratory parameters in substantially the same manners described above.

19 Claims, 10 Drawing Sheets

(56) References Cited

U.S. PATENT DOCUMENTS

2016/0038697 A1 2/2016 Johnson et al.

OTHER PUBLICATIONS

Johnson et al., "Perturbation Device for Noninvasive Measurement of Airway Resistance", Medical Instrumentation 8(2), Mar. 1974.
Johnson et al., "Validation of airflow perturbation device resistance measurements in excised sheep lungs", Institute of Physics Publishing, Physiological Measurement, May 10, 2004, pp. 679-690.
Johnson et. al., "Airflow Perturbation Device for Measuring Airways Resistance of Humans and Animals", IEEE Transactions on Biomedical Engineering, vol. BME-31, No. 9, Sep. 1984, pp. 622-626.
Coursey et al., "Comparison of Expiratory Isovolume Pressure-Flow Curves With the Stop-Flow Versus the Esophageal-Balloon Method", Respiratory Care, Jul. 2011, vol. 56, No. 7, pp. 969-975.

\* cited by examiner

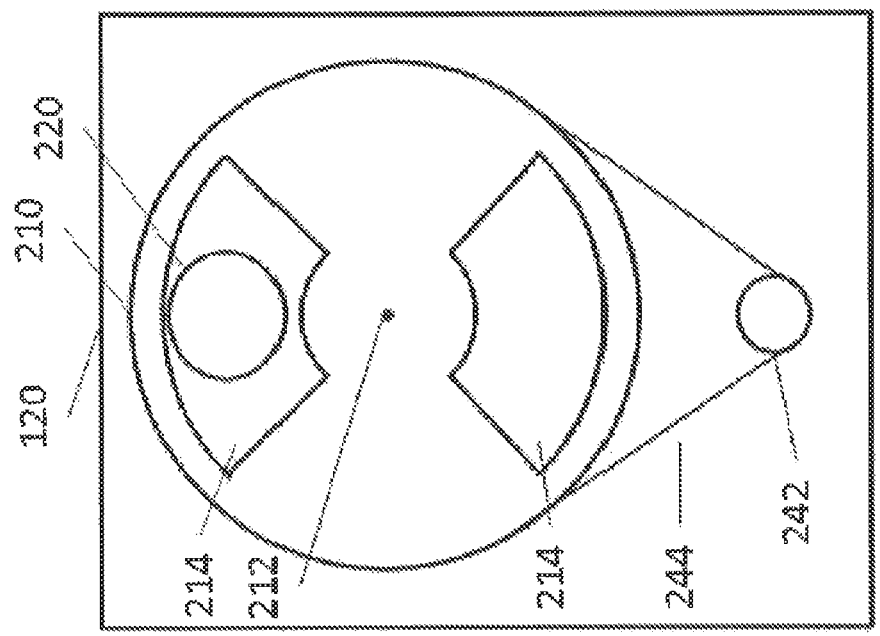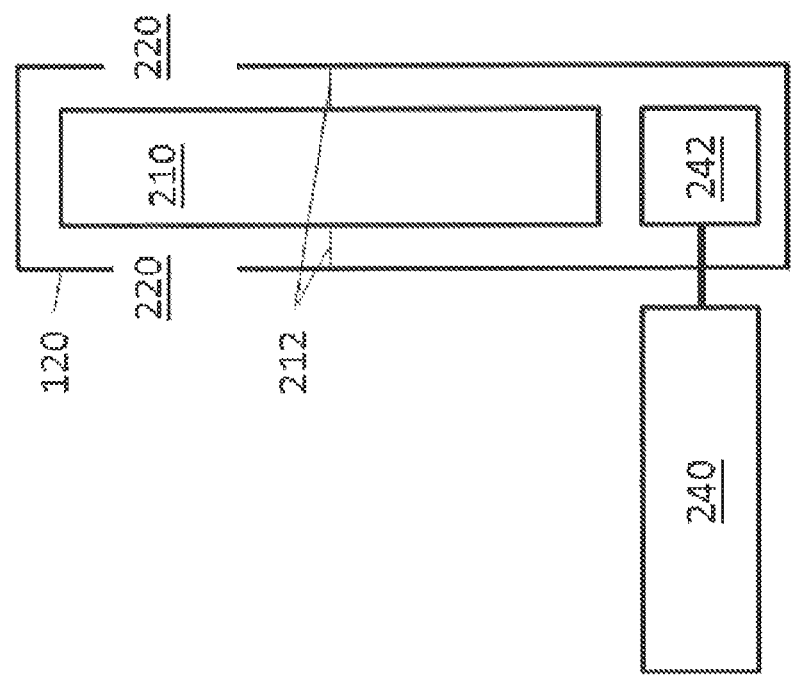

MEASURING RESPIRATORY MECHANICS PARAMETERS USING PERTURBATIONS

CROSS-REFERENCE TO RELATED APPLICATIONS

This application claims the benefit of U.S. Provisional Patent Application No. 62/033,506, titled "Measuring Respiratory Mechanics Parameters Using Perturbations" and filed on Aug. 5, 2014, which is incorporated herein by reference in its entirety.

BACKGROUND

Present invention embodiments relate to measuring parameters of respiratory mechanics, and more specifically, to techniques for measuring respiratory resistance, compliance, and inertance using an airflow perturbation device (APD).

The respiratory system at rest is dominated by two physical components: resistance and compliance. Resistance is the relationship between pressure and flow rate, compliance is the relationship between lung volume and pressure. Both of these components are useful for disease detection, and they may be related. In normal lungs, higher values of resistance usually accompany lower values of compliance, in diseased lungs, both may increase together, although this is not always the case.

Airflow perturbation devices were developed to measure resistance. An APD periodically inserts a resistance in the flow pathway from the mouth. Typically, this is done using a rotating wheel with open and closed segments. As the wheel rotates, changes (or perturbations) occur in both mouth pressure and respiratory flow. The depths of these perturbations depend on the respiratory resistance of the person breathing through the APD and the resistance of the APD itself.

Primary measurements made by the APD are mouth pressure, measured at the location of the APD closest to the mouth, and respiratory airflow, measured with a flowmeter in the flow pathway. The mouth pressure measurement represents the difference in pressure between the mouth and the atmosphere. If the side of the APD distal to the mouth is open to the atmosphere, the mouth pressure measurement divided by the flow measurement represents the resistance of the APD. Thus, APD resistance is known and respiratory resistance of the person using the APD can be inferred. Resistance of the respiratory system may be obtained non-invasively by dividing the mouth pressure perturbation magnitude by the flow perturbation magnitude.

Measurements with the APD have been confirmed to be those of respiratory resistances, consisting of the airways, lung tissue, and chest wall resistance components. APD resistance measurements have been compared to resistance measurements made with the body plethysmograph, forced oscillation, and esophageal balloon.

However, conventional APD techniques do not provide a measurement of compliance. Compliance depends on volume, whereas resistance depends on flow. If the flow rate perturbation is sinusoidal, then the corresponding volume perturbation may in principal be obtained by integrating sinusoidal flow. The result is a cosine function 90° out-of-phase with the sinusoidal flow. This is the manner in which resistance and compliance are obtained using the forced oscillation (FO) method of pulmonary testing and its variants, forced random noise (FRN) and impulse oscillometry (IOS). But compliance cannot be obtained in this way with the APD. The APD perturbation is not completely sinusoidal, nor does it need to be sinusoidal. Moreover, the APD makes measurements in the time domain with time series data, but the detection of phase angles requires frequency domain measurements based on complete sine waves. The APD mouth pressure and flow measurements are always in phase because all APD elements between the mouth and the APD opening exposed to the atmosphere are resistive in nature. These characteristics provide the APD with rapid response and the ability to separate resistance during the inhalation phase of breathing from resistance during the exhalation phase, but render the APD poorly suited for measuring a phase difference between pressure and flow to determine compliance.

SUMMARY

According to one embodiment of the present invention, a method of determining respiratory parameters comprises determining a ratio of pressure changes to flow changes induced in the breathing of a patient by an airflow perturbation device at each of a plurality of perturbation frequencies to form a dataset, Resistance, compliance, and inertance parameters of a model of a respiratory system are determined by comparing a predicted frequency dependence of the model to the dataset. Embodiments of the present invention further include a system and computer program product for determining respiratory parameters in substantially the same manners described above.

BRIEF DESCRIPTION OF THE SEVERAL VIEWS OF THE DRAWINGS

Generally, like reference numerals in the various figures are utilized to designate like components.

FIGS. 2A and 2B are block diagrams of an example perturbation mechanism in cross-sectional side-view and front view respectively according to an embodiment of the present invention.

DETAILED DESCRIPTION

Present invention embodiments provide techniques to determine a plurality of respiratory parameters (e.g., resistance, compliance, and inertance) by operating an airflow perturbation device (APD) at a plurality of different frequencies. The respiratory parameters may be determined by comparing a model of the respiratory system to APD results for the different frequencies.

Figure 1:
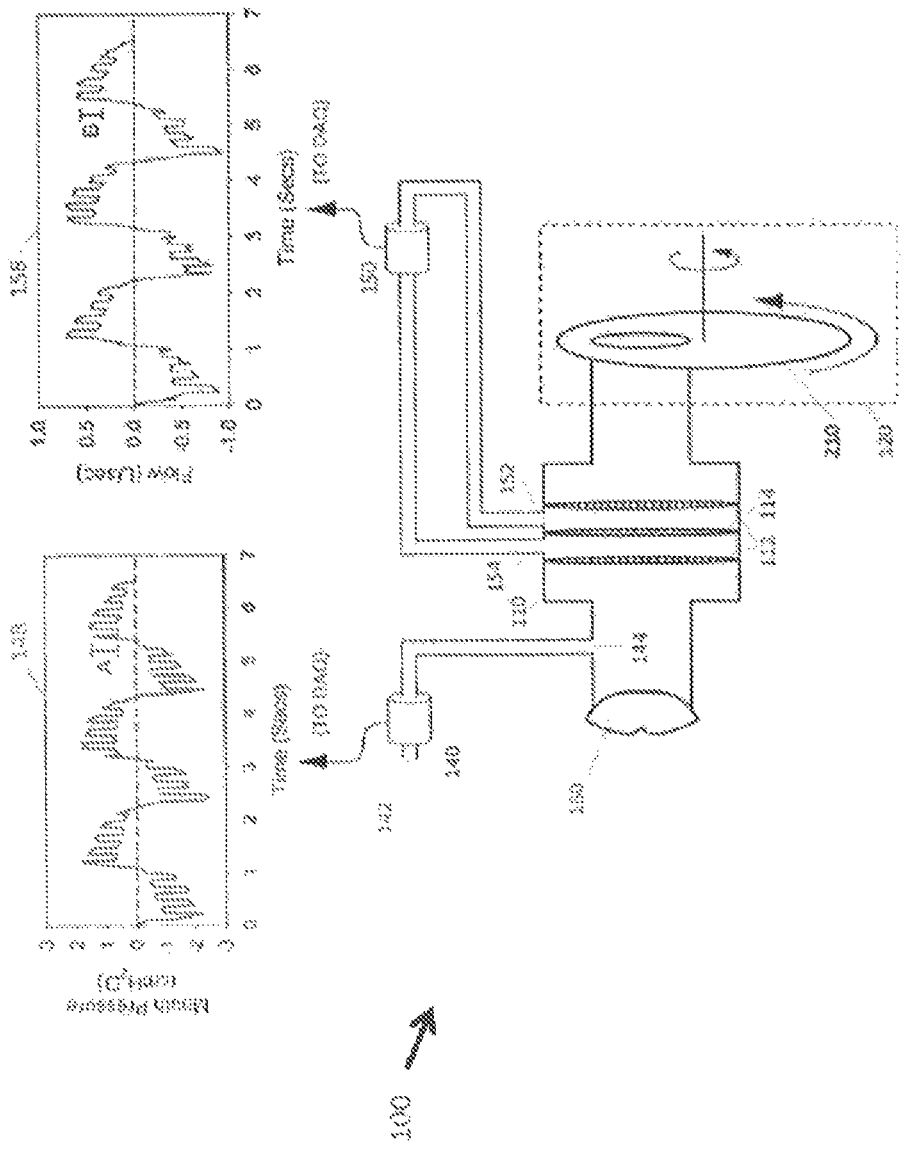
FIG. 1 is a diagrammatic illustration of an example airflow perturbation device according to an embodiment of the present invention.

An example APD for measuring respiratory parameters according to an embodiment of the present invention is illustrated in FIG. 1. In particular, APD 100 comprises pneumotachometer 110, perturbation mechanism 120, pressure sensor 140, pressure tap 144, flow sensor 150, and patient interface 160. Aspects of the APD may operate in manners similar to corresponding aspects described in U.S. Pat. No. 6,066,101, which is hereby incorporated by reference in its entirety.

Patient interface 160 provides an aperture via which a patient may breathe through the APD. Example patient interfaces may include a mouthpiece, an oronasal mask, or the like. Pressure sensor 140 measures the pressure at or near the patient's mouth, via pressure tap 144, relative to another location 142 (e.g., the atmosphere). By way of example, perturbation mechanism 120 may be implemented using a rotating wheel 210 with open and closed segments.

Pneumotachometer 110 and flow sensor 150 measure airflow to and from the patient through the APD. Pneumotachometer 110 comprises airflow resistance 114 (e.g., a fine metal mesh, an array of capillaries, etc.) and may include airflow elements 112 to facilitate laminar airflow across airflow resistance 114. In one embodiment, airflow elements 112 are meshes disposed before and after airflow resistance 114. Pneumotachometer 110 further comprises pressure taps 152 and 154 disposed with respect to the patient substantially on the distal and proximal side, respectively, of airflow resistance 114. Flow sensor 150 may be implemented using a differential pressure sensor to measure the difference in pressure across airflow resistance 114 using pressure taps 152 and 154. This pressure difference is related to the airflow across airflow resistance 114. The pressure-airflow relationship may be modeled as a proportional or linear relationship, and may be calibrated using standard techniques.

Signals from pressure sensor 140 and flow sensor 150 may be sent to a data acquisition system. Example data from pressure sensor 140 and flow sensor 150 over time are depicted in graphs 148 and 158, respectively. The larger period structure depicted in the graphs corresponds to the patient's inhalations and exhalations. The perturbation mechanism induces the smaller time-scale structure with resulting changes in the mouth pressure having a typical magnitude indicated by A, and the corresponding changes in the air flow having a typical magnitude indicated by B. The ratio of a pressure change (e.g., A) to a flow change (e.g., B) for a given perturbation is referred to as $R_{APD}$. According to an embodiment of the present invention, $R_{APD}$ may be used as an estimate of the magnitude of the patient's respiratory impedance.

An example perturbation mechanism 120 is illustrated in FIGS. 2A and 2B in cross-sectional side-view and front view, respectively, according to an embodiment of the present invention. In particular, the perturbation mechanism may comprise wheel 210 disposed between opposing apertures 220. Air flowing through the APD passes into perturbation mechanism 120 through a first aperture 220, across wheel 210, and out of perturbation mechanism 120 through a second aperture 220. Wheel 210 is rotatable about shaft 212 and comprises regions of different airflow resistance such that the rotating wheel presents periodically varying resistance to the airflow between the patient and atmosphere. For example, wheel 120 may comprise a screen containing at least one open region 214 having a size and location to substantially cover apertures 220 during a portion of the wheel's rotation. Alternatively, region 214 may be screened and the remainder of the wheel may be substantially open or have a screen of another gauge than region 214 to provide a different airflow resistance. Alternatively, the wheel may comprise one or more solid regions that block the airflow.

Rotation of wheel 210 may be driven by motor 240, using pulley 242, and drive belt 244. Motor 240 may be a commercial or custom variable frequency drive. The motor may be contained within a sealed APD housing. Power for the motor may be supplied by batteries residing within the housing. Alternatively, the APD housing may be sealed around a pass-through for a power chord to provide power from an external source. In addition, the motor may couple to an external control signal (e.g., an electrical signal) or a mechanical actuator to control the drive frequency.

In alternative embodiments, perturbations to the airflow may be produced in a manner other than with a wheel (for instance, by pinching a tube or using a shutter). In an embodiment using a pinching mechanism, the mechanism may be configured to pinch a tube at most partly closed in order to ensure a pathway in the event the mechanism fails. A pinching mechanism may be implemented using an electrical function generator and electro sensitive material that contracts as applied voltage increases, or in any other electrical or mechanical manner. In an embodiment using a shutter mechanism, the shutters may be implemented using screens to avoid complete blockage of the airflow. In any embodiment, the perturbation mechanism may include a plurality (e.g., two, three, etc.) of pathways (e.g., tubes), some or all of which are perturbed (e.g., pinched or obstructed by a shutter or wheel).

Figure 3:
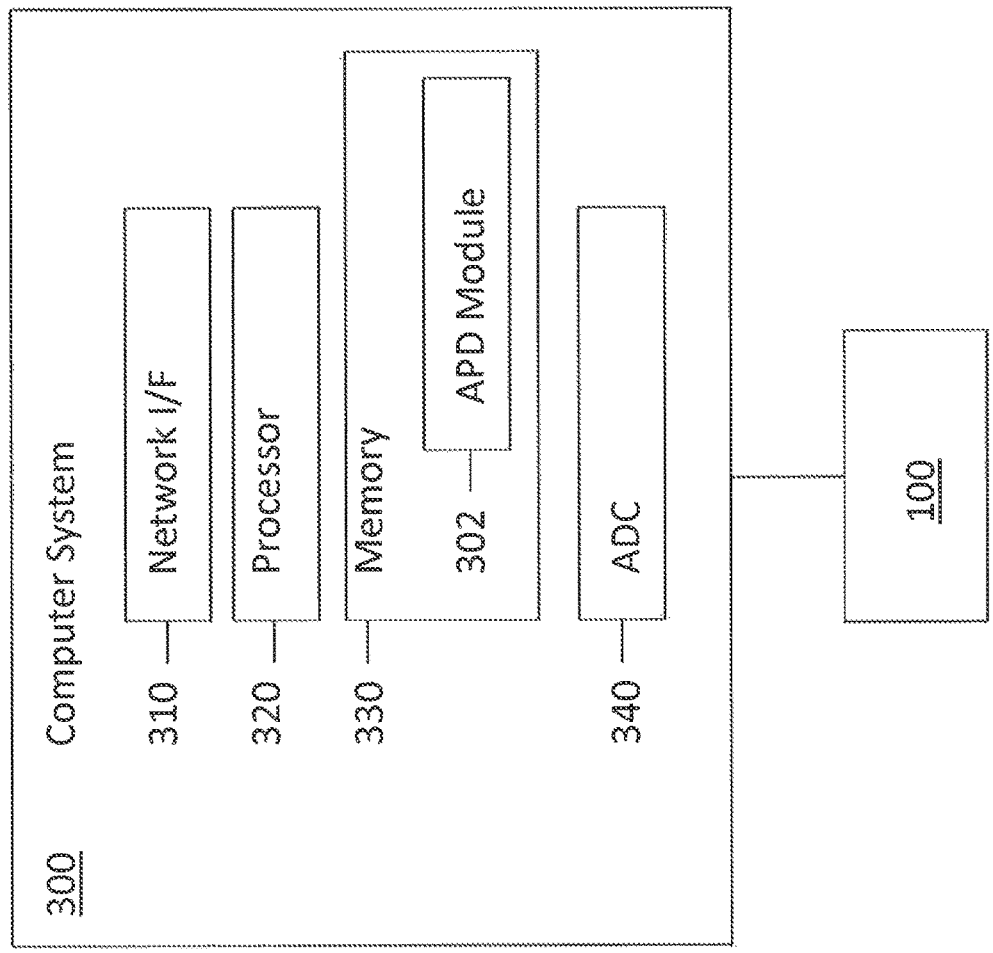
FIG. 3 is a block diagram of an example computing system for data acquisition and analysis according to an embodiment of the present invention.

An example computing system for data acquisition and analysis according to an embodiment of the present invention is illustrated in FIG. 3. In particular, computing system 300 may be implemented by a conventional or other computer system preferably equipped with a display or monitor, a base (e.g., including at least one processor 320, memories 330, analog-to-digital converter (ADC) 340, and/or other external or internal network interface or communications devices 310 (e.g., modem, network cards, etc.)), optional input devices (e.g., a keyboard, mouse, or other input device), and any commercially available and custom software (e.g., APD module 302 software, database software etc.)).

APD module 302 may include one or more modules or units (e.g., ApplyCalibration module, FindPerturbations module, GetVirtualData module, CalcResistance module, SetFrequency module, FitData module, SolveParameters module, Display module, etc.) to perform the various functions of present invention embodiments described below (e.g., calibrating transducer signals, detecting begin and end points of perturbations, interpolating between perturbation begin and end points, calculating $R_{APD}$, varying the perturbation frequency, fitting a parameterized curve, solving for respiratory parameters, etc.), may be implemented by any combination of any quantity of software and/or hardware modules or units, and may reside within memory 330 of computing system 300 for execution by processor 320. The APD module may be implemented across plural computing systems. The computing system(s) may present any graphical user (e.g., GUI, etc.) or other interface (e.g., command line prompts, menu screens, etc.) to receive commands from users and interact with the APD module, APD, and/or other modules, devices, or services.

Computing system 300 communicates with APD 100 to receive signals from pressure sensor 140 and flow sensor 150, and may communicate with other systems (e.g., database systems, client systems, server systems, etc.) over a network implemented by any number of any suitable communications media (e.g., wide area network (WAN), local area network (LAN), Internet, intranet, etc.). In addition, computing system 300 may communicate with motor 240 (e.g., via a control signal line) to control the drive frequency. Computing system 300 may utilize any local or remote data sources implemented by any conventional information storage system (e.g., relational database, file system server, etc.).

Figure 4:
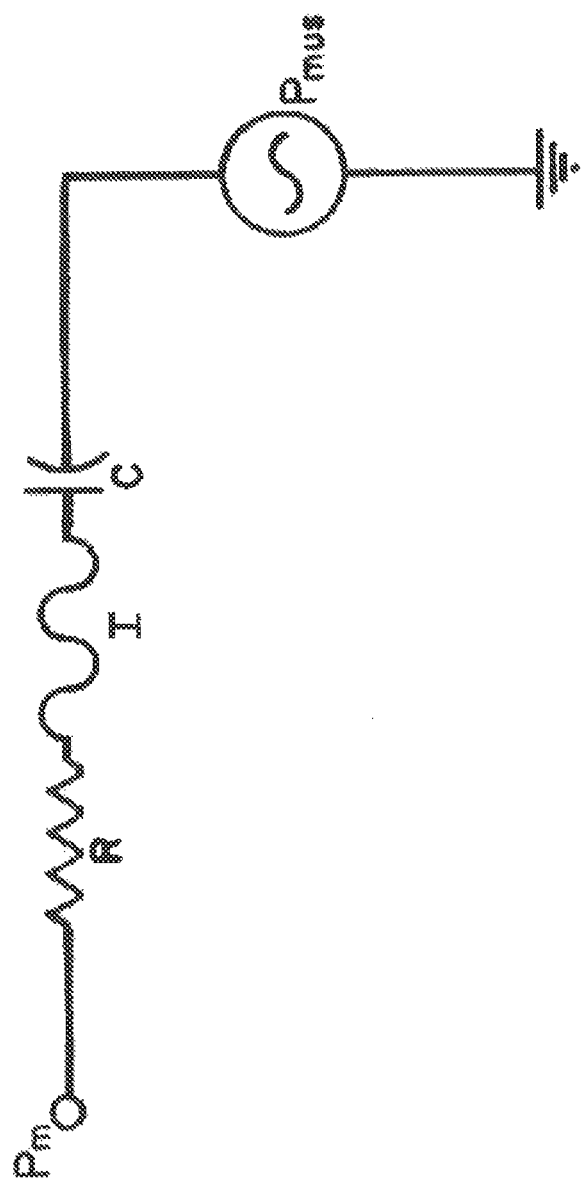
FIG. 4 is a diagram of an example model of a respiratory system according to an embodiment of the present invention.

A model of the respiratory system is shown in diagram FIG. 4. There are three elements in this model: a resistance (R), a compliance (C), and an inertance (I). The resistance is a flow-limiting element; the greater the resistance, the less the flow for any given respiratory muscle pressure. Conversely, maintenance of a given flow requires higher pressure if the resistance is greater. Resistance is of primary interest to pulmonary health. It increases during various diseased states, such as asthma or chronic obstructive pulmonary disease (COPD). This can be a life-Threatening condition.

Respiratory compliance may also be of interest. Compliance is a measure of the relationship between lung volume and pressure. Compliance acts in a similar manner to a balloon. When the lung inflates, its pressure rises. Just as with a balloon, this pressure can be used to expel gas from the lung. Thus, compliance stores an amount of energy proportional to the product of pressure and volume, but compliance, unlike resistance, does not dissipate energy. Compliance can increase in certain diseased conditions, such as COPD.

Inertance is a measure of the inertia of airflow and lung tissue movement, and is the ratio of pressure and rate of change of flow. Inertance, like compliance, is an energy-storage element. Inertance is usually of little interest at normal breathing frequencies, but may be relevant in cases of high-frequency ventilation or sudden lung flow change events.

If the respiratory system has a sinusoidal flow perturbation imposed upon the normal breathing waveform, then there will be a resulting perturbation concomitantly occurring in the mouth pressure. The resistance element causes a mouth pressure perturbation in phase with the flow perturbation. Compliance causes a mouth pressure perturbation lagging 90° from the flow perturbation. Inertance causes a mouth pressure perturbation that leads the flow perturbation by 90°. In other words, if a sinusoidal flow perturbation is imposed, resistance results in a sinusoidal mouth pressure perturbation, compliance results in a negative cosinusoidal mouth pressure perturbation, and inertance results in a cosinusoidal mouth pressure perturbation. A combination of these three elements results in a phase angle between pressure and flow somewhere between 90° and −90°.

The APD does not impose a sinusoidal flow perturbation on the breathing waveform. Instead, it uses an imposed resistance change that has a similar effect. The APD is only a resistive device, and a phase angle cannot be developed across a pure resistance. As a result, the APD does not directly measure the phase difference between pressure and flow. Rather, according to an embodiment of the present invention, respiratory parameters may be determined with the APD based on variation in $R_{APD}$ with perturbation frequency.

Impedance is the general term relating pressure to flow in a mechanical flow system. Impedance can include effects of resistance, compliance, and inertance. Impedance Z is defined as $$Z=p/V',$$

where p represents the pressure and the V' represents the flow (e.g., the rate of change of lung volume). The quantities p and V' may be complex values and may vary with time t; e.g., p and V' may vary in proportion to $e^{j\omega t}$ where j is the imaginary unit $\sqrt{-1}$, and ω is the angular frequency. The physical pressure is the real part of p, denoted Re(p). The physical flow is the real part of V', denoted Re(V').

Impedance for a resistance element is $$Z_R=R=Re(p)/Re(V').$$

Impedance for a compliance element is $$Z_C=X_C=1/(j\omega C)=-j/(\omega C)$$

where $X_C$ is referred to as the compliance reactance, and C is the compliance.

Impedance for an inertance element is $$Z_I=X_I=j\omega I$$

where $X_I$ is referred to as the inertance reactance, and I is the inertance.

Figure 5:
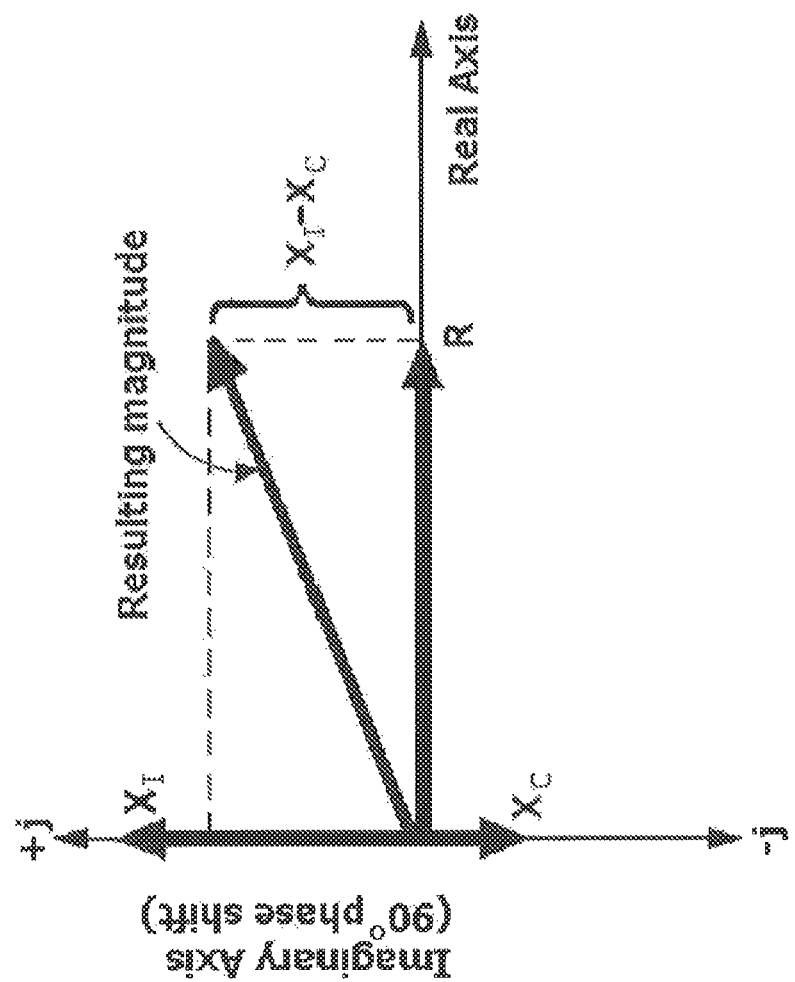
FIG. 5 is a phase diagram of impedance components of a respiratory system according to an embodiment of the present invention.

A phase plane plot showing relationships of the impedance components R, $X_C$, and $X_I$ is illustrated in FIG. 5. The imaginary axis denotes a 90° phase shift from the original perturbation. Both $X_C$ and $X_I$ lie along the imaginary axis, with $X_I$ in the +j direction and $X_C$ lying along the direction. R has no phase shift and so lies along the real axis. Combination of all three components is accomplished vectorially, affecting both the magnitude and phase angle of the resultant. From the phase plane plot, it can be seen that the resultant total impedance is the vectorial combination of the three individual components $Z_R$, $Z_C$, and $Z_I$, and has a magnitude $$Z_{TOT}=[Z_R^2+|Z_C+Z_I|^2]^{1/2}=[R^2+(\omega I-1/(\omega C))^2]^{1/2}.$$

The quantity $R_{APD}$ determined by the APD is a measure of the magnitude $Z_{TOT}$.

Figure 6:
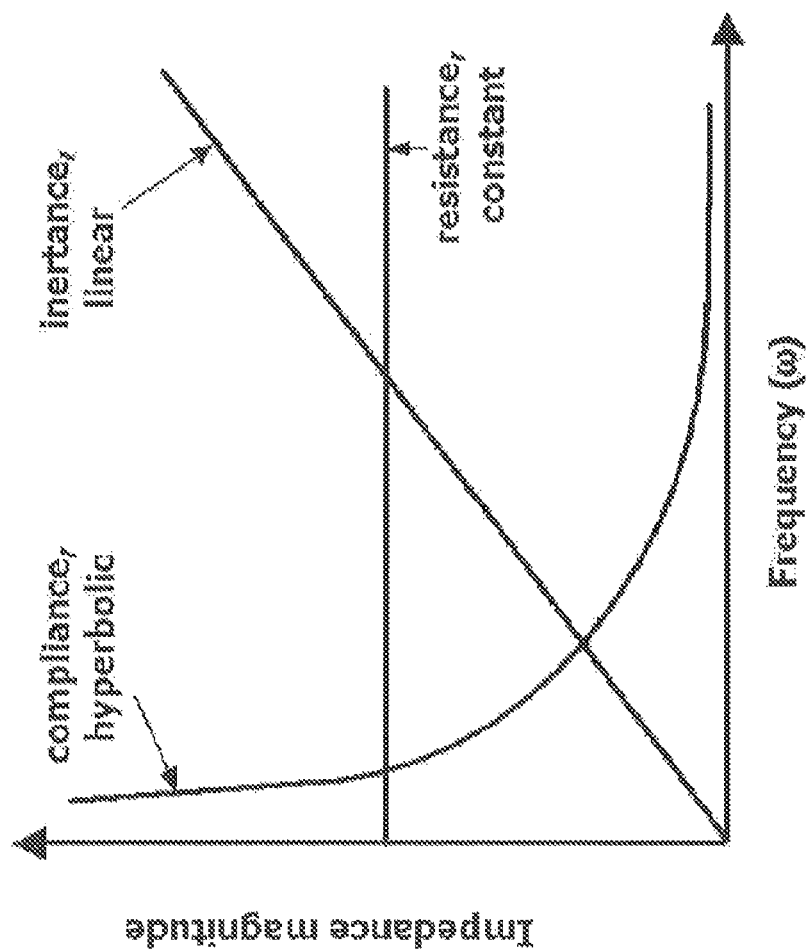
FIG. 6 is a graph depicting magnitudes of impedance components as functions of frequency according to an embodiment of the present invention.

The dependence of $Z_R$, $Z_C$, and $Z_I$ as a function of angular frequency is illustrated in FIG. 6. $Z_R$ is constant (no change with frequency). The plot of $Z_C$ versus frequency is a hyperbola ($Z_C$ varies inversely with frequency). $Z_I$ is a straight, sloped line (direct dependence on frequency).

Figure 7:
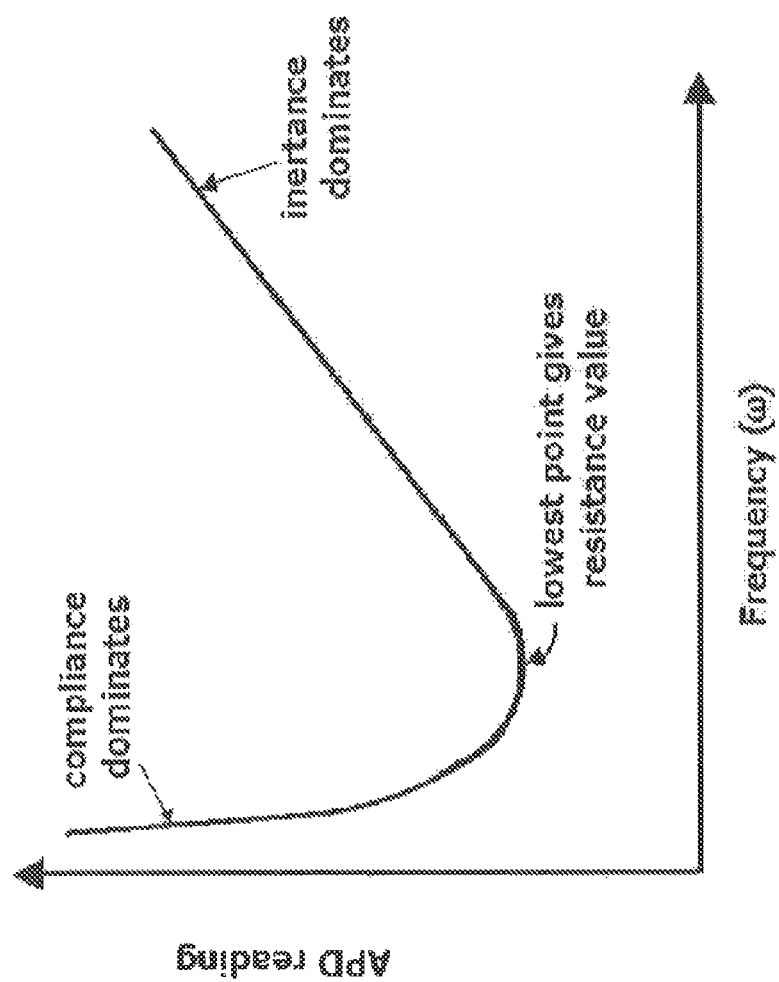
FIG. 7 is a graph depicting values of APD results or total impedance magnitudes as a function of frequency according to an embodiment of the present invention.

The dependence of the magnitude $Z_{TOT}$ as a function of frequency is illustrated in FIG. 7. At low frequencies, $X_C$ dominates and $Z_{TOT}$ decreases with frequency. At high frequencies, $X_I$ dominates and $Z_{TOT}$ increases with frequency. At the minimum point, $X_C=-X_I$, and R is the only component to contribute to $R_{APD}$.

Working with $Z_{TOT}^2$ avoids having to take a square root:

$$\begin{aligned}Z_{TOT}^2 &= R^2 + (j\omega I - j/\omega C)^2 \\ &= R^2 + j^2\omega^2 I^2 - 2j^2(\omega I/\omega C) + j^2/\omega^2 C^2 \\ &= R^2 - \omega^2 I^2 + 2(I/C) - 1/\omega^2 C^2.\end{aligned}$$

Multiplying by $(1/\omega^2)$ gives $$Z_{TOT}^2/\omega^2 = -1/\omega^4 C + (R^2 + 2I/C)/\omega^2 - I^2.$$

This is a quadratic equation, having the form $$y = a_2 x^2 + a_1 x + a_0$$

where $Z_{TOT}^2/\omega^2$, $x = 1/\omega^2$, $a_0 = -I^2$, $a_1 = R^2 \pm 2I/C$, and $a_2 = -1/C$.

Figure 8:
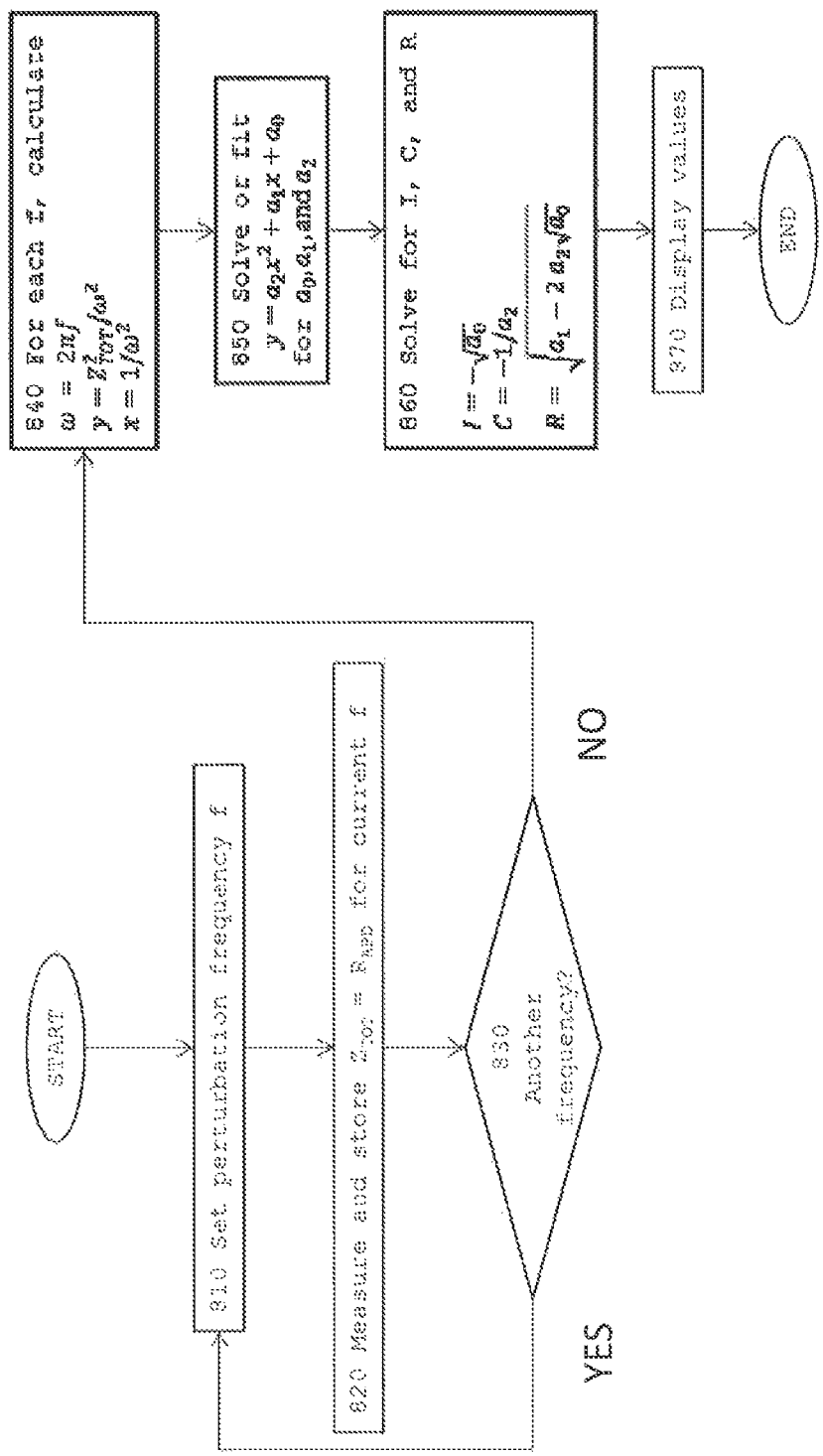
FIG. 8 is a flow diagram illustrating an example manner of using an airflow perturbation device to determine respiratory resistance, compliance, and inertance by scanning different perturbation frequencies according to an embodiment of the present invention.

An example manner of determining respiratory resistance, compliance, and inertance by fitting APD results to a quadratic curve is illustrated in FIG. 8. Initially, APD measurements are collected at different frequencies. For example, the lowest frequency may be in the range of 2-4 Hz and the highest frequency up to 18 Hz or higher. In one embodiment, measurements are collected at ten to sixteen frequencies in 1 Hz increments. Alternatively, the number of different frequencies may be greater or as few as three and may have any spacing. For example, an embodiment may perform measurements at five frequencies evenly spaced on a logarithmic scale.

In particular, at step 810, the perturbation mechanism may be configured to operate with a perturbation frequency f. APD module 302 may send a control signal to motor 240 to set the rotation frequency of wheel 210. Alternatively, an administrator of the test may manually set the frequency (e.g., via a mechanical actuator of a variable speed drive).

At step 820, the APD measures pressure and air flow changes due to perturbations at the current frequency, determines $R_{APD}$ from those changes, and stores the result.

At step 830, the APD module determines whether another frequency remains in the set of frequencies at which to measure $R_{APD}$. If so, processing returns to step 810. Otherwise, processing proceeds to step 840.

At step 840, the APD module calculates $x = 1/\omega^2$ and $y = R_{APD}^2/\omega^2$ where $\omega = 2\pi f$, from the data saved at step 820 for each tested frequency f. At step 850, the APD module fits (or solves) $y = a_2 x^2 + a_1 x + a_0$ to the (x, y) values calculated at step 640 to determine the coefficients $a_0$, $a_1$, and $a_2$. At step 860, the APD module solves for I, C, and R in terms of the coefficients: $I = -\sqrt{a_0}$, $C = -1/a_2$, and $R = \sqrt{a_1 - 2a_2\sqrt{a_0}}$. At step 870, the APD module may display the results, including, the determined values of I, C, and R. In addition, the APD module may determine these three component values separately in the inhalation and exhalation directions.

Figure 9:
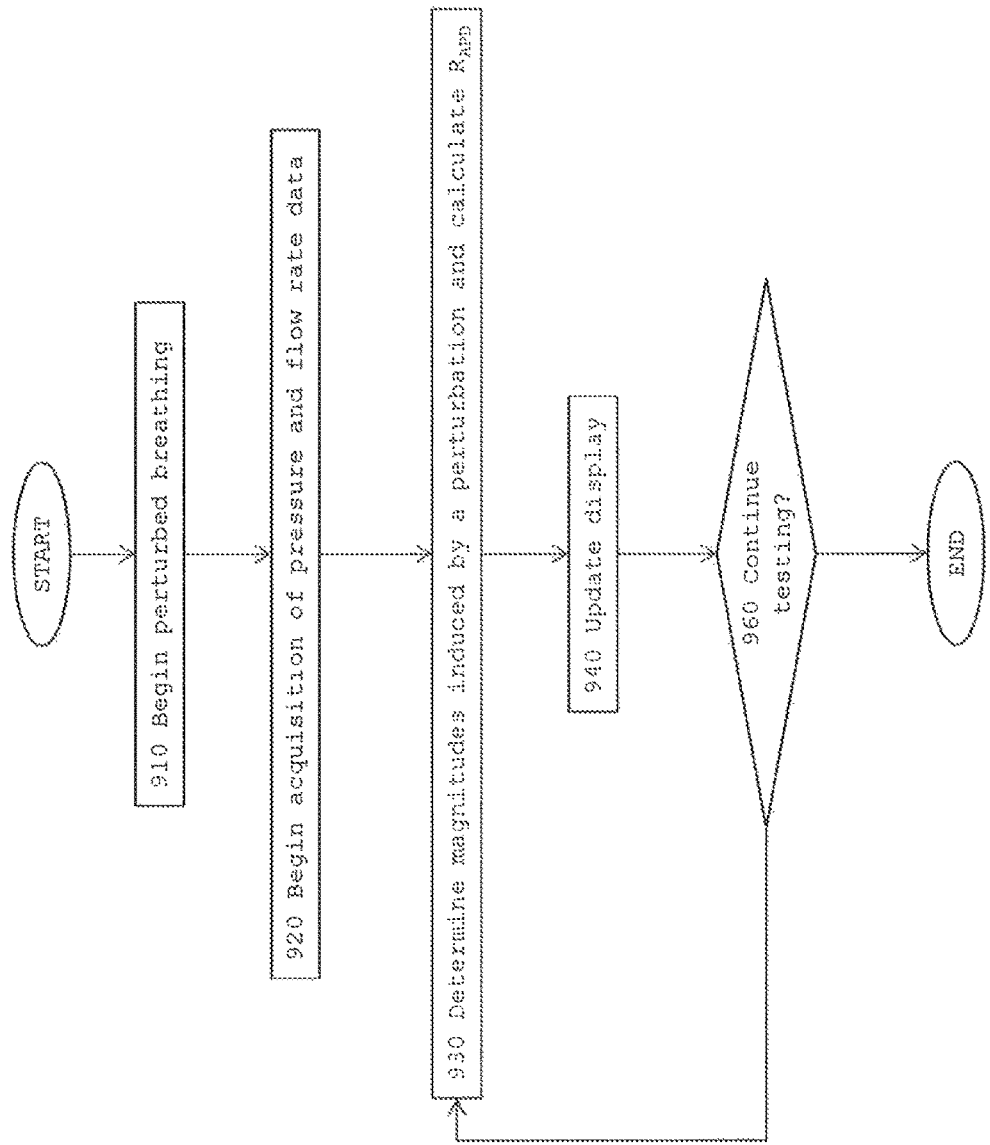
FIG. 9 is a flow diagram illustrating an example manner of estimating an impedance magnitude for a given perturbation frequency according to an embodiment of the present invention.
Figure 10:
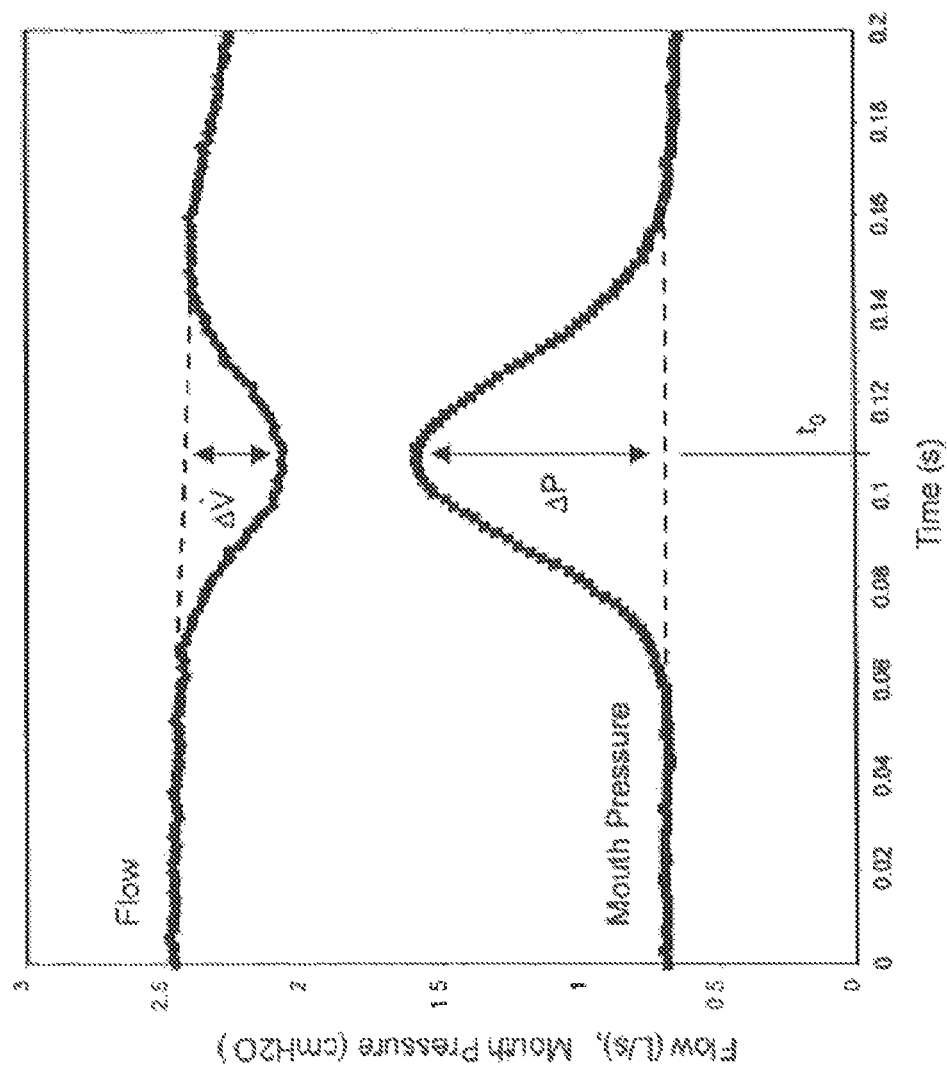
FIG. 10 is an illustration of example pressure and flow signals for an individual perturbation according to an embodiment of the present invention.

An example manner of determining an $R_{APD}$ value for a given perturbation frequency according to an embodiment of the present invention is illustrated in FIGS. 9 and 10. Testing is initiated at step 910. The patient breathes through the APD with the airflow perturbed at the given frequency.

At step 920, acquisition of pressure and flow rate data begins. The pressure transducers of pressure sensor 140 and flow sensor 150 send electrical signals to computer system 300. ABC 140 digitizes the signals. APD module 302 continually monitors and records the digitized signals from the pressure transducers for mouth pressure and pneumotachometer flow sensor. The APD module may apply predetermined calibrations to the data (e.g., converting digitized pressure transducer data from pressure sensor 140 to units of pressure, converting digitized pressure transducer data from flow sensor 150 to units of volume per time based on a measured resistance of airflow resistance 114, etc.).

At step 930. APD module 302 determines the pressure and flow changes due to an individual perturbation and performs a calculation of $R_{APD}$ based on those changes. Typically, the APD module operates in real-time. Example mouth pressure and air flow data for an individual perturbation are illustrated in FIG. 10. The APD module interpolates (e.g., linearly) the mouth pressure and flow rate data between the points when the signals are essentially unperturbed (e.g., when the wheel resistance is zero) immediately preceding the perturbation and immediately following the perturbation. These interpolated signals are referred to as virtual signals and are indicated by the dashed lines in FIG. 10. Changes in mouth pressure and flow rate induced by the perturbation mechanism are measured with respect to the corresponding virtual signals. In particular, the changes may be computed as the observed signal minus the virtual signal. The APD module determines the time ($t_0$) at which the magnitudes of the changes are greatest. The pressure change magnitude (A) and flow change magnitude (B) at $t_0$ may be used to calculate $R_{APD} = A/B$. These results may be separated, based on flow signal polarity, into $R_{APD}$ during inspiration and $R_{APD}$ during expiration. This separation can be useful for determining abnormalities that affect one or another of the breathing phases.

At step 940, the APD module may update the display to indicate the calculated $R_{APD}$. For example, the display may show the most recent respiratory resistance calculation, a list of the most recent respiratory resistance calculations, a graph of the most recent respiratory calculations versus time, or the like. Respiratory resistance is normally calculated once for each perturbation.

At step 960, a determination is made as to whether to continue testing at the current frequency. For example, testing may continue for a predetermined period of time (e.g., 1 minute, 1.5 minutes, etc.). Alternatively testing may continue until a desired accuracy of the $R_{APD}$ measurement is achieved. If the determination is to continue testing, processing returns to step 930, and the next perturbation is detected and analyzed. Otherwise, testing at the current frequency ends.

It will be appreciated that the embodiments described above and illustrated in the drawings represent only a few of the many ways of implementing embodiments for measuring respiratory parameters of patients by performing APD measurements at a variety of different frequencies.

For example, resistance and compliance may be determined with or without directly determining inertance. In general, compliance impedes flow inversely with frequency and magnitude. As frequency increases up to the point at which $R_{APD}$ reaches its minimum, the upstream impedance, comprising resistance and compliance, decreases. That magnifies the effect of the downstream added APD resistance. Both pressure and flow perturbations generally increase as a result. The ratio of pressure and flow perturbations determines the APD measurement $R_{APD}$. Flow perturbations increase proportionality more than pressure perturbations because the flow perturbation is initially smaller than pressure perturbations. Thus APD readings at higher frequencies decrease in magnitude compared to those at lower frequencies, until the minimum $R_{APD}$ is reached.

Impedance of compliance is determined by the inverse of frequency and compliance. Therefore, changes in compliance generally change APD resistance in the same way as changes in frequency. Because there are two variants affecting APD measurements, at least two different frequencies must be used. However, inertance may be taken to have a predetermined value or be constrained by another measurement.

The results may depend on perturbation shape, but as long as perturbation shapes at different frequencies remain consistent, compliance measurements can be made without signal phase differences.

An alternative approach to determining compliance values from signals provided by an APD is to use exponential changes in pressure and flow signals within the perturbation period. If the perturbation were to be made into a square wave, for instance, then responses to the pressure and flow increases and decreases would be exponential curves with time constants given by the product of respiratory resistance and respiratory compliance. This approach provides very rapid resistance and compliance determinations, but uses a more complex perturbation shape and yields a response related to, but not directly obtainable from, an exponential curve. Moreover, the perturbation is formed as resistance in the flow path changes, which may dynamically change the exponential time constant.

Using the APD to measure compliance as well as resistance will give physicians all the tools they need to diagnose common pulmonary diseases. Compliance information can distinguish between pulmonary restrictive and obstructive diseases better than can respiratory resistance. At present, pulmonary compliance is not easily or inexpensively measured, Including pulmonary compliance capability within the APD can become very important for pulmonary function testing of respiratory-impaired individuals.

An embodiment of the present invention may utilize any conventional or other pneumotachometer technology, pressure sensors, and perturbation mechanism (e.g., rotary wheel, shutter, pinch techniques, etc.).

The environment of the present invention embodiments may include any number of computer or other processing systems (e.g., client or end-user systems, server systems, etc.) and storage systems (e.g., file systems, databases, or other repositories), arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., database software, communications software, etc.). These systems may include any types of monitors and input devices (e.g., keyboard, mouse, voice recognition, touch screen, etc.) to enter and/or view information, It is to be understood that the software of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures files databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

What is claimed is:
1. A system for measuring one or more respiratory parameters comprising:
an airflow perturbation device comprising:
a perturbation mechanism to periodically alter air flow resistance in a pathway at a plurality of different perturbation frequencies, wherein the perturbation mechanism includes an air flow path, an obstruction element disposed in the air flow path, and an actuator coupled to the obstruction element to control the obstruction element to obstruct air flow;
a pneumotachometer comprising a flow sensor to measure airflow in the pathway; and
a pressure sensor to measure a pressure in the pathway; and a computing system comprising at least one processor configured to:
control the perturbation mechanism to operate at each of the plurality of different perturbation frequencies in succession;
receive data from the flow sensor and pressure sensor and determine a ratio of pressure changes to flow changes induced by the airflow perturbation device at each of the plurality of different perturbation frequencies to form a dataset of resistance of a respiratory system at each of the plurality of different perturbation frequencies; and
determine at least one respiratory parameter based on variations in the resistance over the different perturbation frequencies by fitting a curve defined by the resistance at each of the different perturbation frequencies to a predicted frequency dependence curve indicating contributions of respiratory parameters to resistance, wherein the at least one respiratory parameter includes a compliance of the respiratory system.

2. The system of claim 1, wherein the at least one processor is further configured to:
display the determined at least one respiratory parameter.

3. The system of claim 1, further comprising:
a control line communicatively coupling the computing system and the perturbation mechanism;
wherein the at least one processor is further configured to control the perturbation mechanism to operate at the plurality of different perturbation frequencies via the control line.

4. The system of claim 1, wherein the perturbation mechanism comprises a variable frequency drive.

5. The system of claim 1, wherein the perturbation mechanism comprises a rotating segmented wheel.

6. The system of claim 1, wherein the perturbation mechanism comprises a selected one of a mechanism for pinching a flexible tube and a shutter.

7. The system of claim 1, wherein determining the ratio of pressure to flow changes comprises determining changes in the pressure and airflow expected in the absence of the induced changes by interpolating signals between perturbations.

8. The system of claim 1, wherein determining the at least one respiratory parameter further comprises:
constraining an inertance of the respiratory system to a predetermined value.

9. The system of claim 1, wherein predicted frequency dependence of the predicted frequency dependence curve comprises a quadratic dependence of a first quantity proportional to a square of a quotient of the ratio and the frequency on a second quantity proportional to a square inverse of the frequency; and the at least one processor is configured to:
determine quadratic coefficients by fitting to the dataset; and
determine at least a resistance and compliance of the respiratory system from the quadratic coefficients.

10. The system of claim 1, wherein the predicted frequency dependence of the predicted frequency dependence curve comprises an exponential response of pressure and flow to perturbations in the pathway, and the exponential response has a time constant given by a product of respiratory resistance and respiratory compliance.

11. A method of measuring a respiratory parameter of a respiratory system comprising:
controlling, via at least one processor, an airflow perturbation device to operate at each of a plurality of different perturbation frequencies in succession and receiving data from the airflow perturbation device, wherein the airflow perturbation device includes:
a perturbation mechanism to periodically alter air flow resistance in a pathway at the plurality of different perturbation frequencies, wherein the perturbation mechanism includes an air flow path, an obstruction element disposed in the air flow path, and an actuator coupled to the obstruction element to control the obstruction element to obstruct air flow;
a pneumotachometer comprising a flow sensor to measure airflow in the pathway; and
a pressure sensor to measure a pressure in the pathway;
determining, via the at least one processor, a ratio of pressure changes to flow changes in the pathway induced by the airflow perturbation device at each of the plurality of different perturbation frequencies to form a dataset of resistance of the respiratory system at each of the plurality of different perturbation frequencies; and
determining, via the at least one processor, at least one respiratory parameter based on variations in the resistance over the different perturbation frequencies by fitting a curve defined by the resistance at each of the different perturbation frequencies to a predicted frequency dependence curve indicating contributions of respiratory parameters to resistance, wherein the at least one respiratory parameter includes a compliance of the respiratory system.

12. The method of claim 11, wherein determining the at least one respiratory parameter includes determining an inertance of the respiratory system.

13. The method of claim 11, wherein determining the at least one respiratory parameter includes constraining an inertance of the respiratory system to a predetermined value.

14. The method of claim 11, wherein the predicted frequency dependence of the predicted frequency dependence curve comprises a quadratic dependence of a first quantity proportional to a square of a quotient of the ratio and the frequency on a second quantity proportional to a square inverse of the frequency; and determining the at least one respiratory parameter comprises:
determining quadratic coefficients by fitting to the dataset; and
determining at least a resistance and compliance of the respiratory system from the quadratic coefficients.

15. The method of claim 11, wherein the plurality of different perturbation frequencies includes at least ten frequencies in the range two hertz to eighteen hertz.

16. The method of claim 11, wherein the plurality of different perturbation frequencies includes at most five frequencies.

17. The method of claim 11, wherein the different perturbation frequencies have non-uniform spacing.

18. The method of claim 11, further comprising:
displaying the determined at least one respiratory parameter.

19. The method of claim 11, wherein the predicted frequency dependence of the predicted frequency dependence curve comprises an exponential response of pressure and flow to perturbations in the pathway, and the exponential response has a time constant given by a product of respiratory resistance and respiratory compliance.

* * * * *